US011135271B2

(12) United States Patent
Kim et al.

(10) Patent No.: US 11,135,271 B2
(45) Date of Patent: Oct. 5, 2021

(54) GLUCAGON DERIVATIVES WITH IMPROVED STABILITY

(71) Applicant: HANMI PHARM. CO., LTD., Hwaseong-si (KR)

(72) Inventors: Jung Kuk Kim, Hwaseong-si (KR); Jong Min Lee, Hwaseong-si (KR); Sang Yun Kim, Hwaseong-si (KR); Sung Min Bae, Hwaseong-si (KR); Sung Youb Jung, Hwaseong-si (KR); Se Chang Kwon, Hwaseong-si (KR)

(73) Assignee: HANMI PHARM. CO., LTD., Hwaseong-si (KR)

( * ) Notice: Subject to any disclaimer, the term of this patent is extended or adjusted under 35 U.S.C. 154(b) by 207 days.

(21) Appl. No.: 15/540,729

(22) PCT Filed: Dec. 30, 2015

(86) PCT No.: PCT/KR2015/014422
§ 371 (c)(1),
(2) Date: Jun. 29, 2017

(87) PCT Pub. No.: WO2016/108586
PCT Pub. Date: Jul. 7, 2016

(65) Prior Publication Data
US 2017/0360892 A1  Dec. 21, 2017

(30) Foreign Application Priority Data

Dec. 30, 2014 (KR) .................. 10-2014-0193800

(51) Int. Cl.
*A61K 38/26* (2006.01)
*C07K 14/605* (2006.01)
*A61K 45/06* (2006.01)

(52) U.S. Cl.
CPC .............. *A61K 38/26* (2013.01); *A61K 45/06* (2013.01); *C07K 14/605* (2013.01)

(58) Field of Classification Search
CPC ............................ A61K 38/26; C07K 14/605
See application file for complete search history.

(56) References Cited

U.S. PATENT DOCUMENTS

| 5,408,037 | A  | 4/1995  | Smith et al. |
| 7,994,122 | B2 | 8/2011  | Riber et al. |
| 8,450,270 | B2 | 5/2013  | DiMarchi et al. |
| 8,454,971 | B2 | 6/2013  | Day et al. |
| 8,507,428 | B2 | 8/2013  | DiMarchi et al. |
| 8,703,701 | B2 | 4/2014  | DiMarchi |
| 2006/0275254 | A1 | 12/2006 | Kim et al. |
| 2009/0111739 | A1 | 4/2009  | Kajihara et al. |
| 2010/0105877 | A1 | 4/2010  | Song et al. |
| 2010/0190699 | A1 | 7/2010  | Dimarchi et al. |
| 2010/0190701 | A1 | 7/2010  | Day et al. |
| 2010/0330108 | A1 | 12/2010 | Song et al. |
| 2011/0082079 | A1 | 4/2011  | Spetzler et al. |
| 2012/0165503 | A1 | 6/2012  | Carrington et al. |
| 2012/0288511 | A1 | 11/2012 | Dimarchi |
| 2012/0329715 | A1 | 12/2012 | Greig et al. |
| 2013/0116173 | A1 | 5/2013  | DiMarchi et al. |
| 2013/0143798 | A1 | 6/2013  | Lau et al. |
| 2013/0203659 | A1 | 8/2013  | Miranda et al. |
| 2014/0011738 | A1 | 1/2014  | DiMarchi |
| 2014/0128318 | A1* | 5/2014 | Jung .................... C07K 14/705 514/4.8 |
| 2015/0164997 | A1 | 6/2015  | Haack et al. |
| 2015/0368310 | A1 | 12/2015 | DiMarchi et al. |
| 2018/0311315 | A1 | 11/2018 | Oh et al. |

FOREIGN PATENT DOCUMENTS

| CN | 102892425 A | 1/2013 |
| CN | 103732618 A | 4/2014 |
| CO | NC2017/0006308 | 9/2017 |
| EA | 201791333 A1 | 12/2017 |
| JP | 2014-507402 A | 3/2014 |
| JP | 5476304 B2 | 4/2014 |
| JP | 2015-521622 A | 7/2015 |
| KR | 10-2009-0096498 A | 9/2009 |
| KR | 10-2012-0010146 A | 2/2012 |
| KR | 10-2012-0052973 A | 5/2012 |
| KR | 10-2012-0068755 | 6/2012 |

(Continued)

OTHER PUBLICATIONS

The Isoelctric Point, Chapter 23.4. Publication update year 2014.*
Perfetti et al., Eur. J. Endocr. 143, 717-725, 2000.*
Gutniak et al., New England J. Med. 30 326:1316-1322, 1992.*
Unson et al., Arch. Biochem and Biophys. 300: 747-750, 1993.*
Krstenansky et al. (Pept: Struct. Funct., Proc. Am. Pept. Symp. 9th, (1985), 591-594.*
Joseph Chabenne et al., "A glucagon analog chemically stabilized for immediate treatment of life-threatening hypoglycemia," Molecular Metabolism, Jan. 2014, pp. 293-300, vol. 3.
Kevin L. Shaw et al., "The effect of net charge on the solubility, activity, and stability of ribonuclease SA," Protein Science, 2001, pp. 1206-1215, vol. 10.

(Continued)

*Primary Examiner* — Gyan Chandra
(74) *Attorney, Agent, or Firm* — Sughrue Mion, PLLC

(57) ABSTRACT

The present invention relates to a novel glucagon derivative peptide, and a composition for preventing or treating hypoglycemia containing the novel glucagon derivative peptide as an active ingredient. The glucagon derivative according to the present invention has improved physical properties due to the change in isoelectric point (pI) while being capable of maintaining an activity on glucagon receptors, and thus can improve patient compliance when used as a hypoglycemic agent, and is also suitable for administration in combination with other anti-obesity agents. Accordingly, the glucagon derivative according to the present invention can be effectively used for the prevention and treatment of hypoglycemia and obesity.

10 Claims, No Drawings

Specification includes a Sequence Listing.

(56) References Cited

FOREIGN PATENT DOCUMENTS

| | | |
|---|---|---|
| KR | 10-2013-0018410 A | 2/2013 |
| KR | 10-2014-0018462 A | 2/2014 |
| KR | 10-1382593 B1 | 4/2014 |
| KR | 10-2015-0096398 A | 8/2015 |
| KR | 10-2015-0096433 A | 8/2015 |
| MA | 40709 A1 | 12/2017 |
| MA | 41887 A1 | 12/2018 |
| TW | 201307380 A1 | 2/2013 |
| WO | 96/16196 A2 | 5/1996 |
| WO | 96/16196 A3 | 5/1996 |
| WO | 96/32478 A1 | 10/1996 |
| WO | 97/34631 A1 | 9/1997 |
| WO | 0183527 A2 | 11/2001 |
| WO | 2004/093823 A2 | 11/2004 |
| WO | 2008101017 A2 | 8/2008 |
| WO | 2009099763 A1 | 8/2009 |
| WO | 2010/011439 A2 | 1/2010 |
| WO | 2010/096052 A1 | 8/2010 |
| WO | 2010148089 A1 | 12/2010 |
| WO | 2011038900 A2 | 4/2011 |
| WO | 2011/075393 | 6/2011 |
| WO | 2011/088837 A1 | 7/2011 |
| WO | 2011/117415 A1 | 9/2011 |
| WO | 2011143208 A1 | 11/2011 |
| WO | 2012/011752 A2 | 1/2012 |
| WO | 2012/088116 A2 | 6/2012 |
| WO | 2012/158965 A2 | 11/2012 |
| WO | 2012150503 A2 | 11/2012 |
| WO | 2012/169798 A2 | 12/2012 |
| WO | 2012/173422 A1 | 12/2012 |
| WO | 2013/004983 A1 | 1/2013 |
| WO | 2013/074910 A1 | 5/2013 |
| WO | 2013/192129 A1 | 12/2013 |
| WO | 2013/192130 A1 | 12/2013 |
| WO | 2014/017843 A1 | 1/2014 |
| WO | 2014/017845 A2 | 1/2014 |
| WO | 2014049610 A2 | 4/2014 |
| WO | 2014/073842 A1 | 5/2014 |
| WO | 2014/073845 A1 | 5/2014 |
| WO | 2014/081864 A1 | 5/2014 |
| WO | 2014/081872 A1 | 5/2014 |
| WO | 2014/096145 A1 | 6/2014 |
| WO | 2014/096150 | 6/2014 |
| WO | 2014/170496 A1 | 10/2014 |
| WO | 2015022420 A1 | 2/2015 |
| WO | 2015/183054 A1 | 12/2015 |
| WO | 2016/043533 A1 | 3/2016 |
| WO | 2016/049190 A1 | 3/2016 |
| WO | 2016/108586 A1 | 7/2016 |
| WO | 2017/003191 A1 | 1/2017 |

OTHER PUBLICATIONS

International Search Report of PCT/KR2015/014422 dated Apr. 14, 2016.
Brian Finan, et al., "A rationally designed monomeric peptide triagonist corrects obesity and diabetes in rodents", Nat Med., Jan. 2015, 1-13 pages, vol. 21, No. 1. (15 pages total).
Daniel J. Drucker, et al., "The Incretin system: glucagon-like peptide-1 receptor agonists and dipeptidyl peptidase-4 inhibitors in type 2 diabetes", The Lancet, Nov. 11, 2006, pp. 1696-1705, vol. 368.
International Searching Authority; International Search Report for PCT/KR2016/015555 dated Apr. 10, 2017 [PCT/ISA/210].
Jonathan W. Day, et al., "A new glucagon and GLP-1 co-agonist eliminates obesity in rodents", Nature Chemical Biology, Oct. 2009, pp. 749-757, vol. 5, No. 10.
Yahiya Y. Syed, et al., "Exenatide Extended-Release: An Updated Review of Its Use in Type 2 Diabetes Mellitus", Drugs, Jun. 2015, 12 pages, vol. 10.
International Searching Authority; International Search Report for PCT/KR2016/015554 dated Apr. 10, 2017 [PCT/ISA/210].
Korean Intellectual Property Office, Communication dated Jul. 11, 2018, issued in Korean Application No. 10-2016-0183499.
Korean Intellectual Property Office, Communication dated Jul. 11, 2018, issued in Korean Application No. 10-2016-0183500.
Australian Patent Office; Communication dated Jul. 31, 2018 in application No. 2016382393.
Australian Patent Office; Communication dated Jul. 31, 2018 in application No. 2016382394.
Australian Patent Office; Communication dated Feb. 7, 2019 in application No. 2017289014.
Cecilia G. Unson et al., "The Role of Histidine-1 in Glucagon Action", Archives of Biochemistry and Biophysics, vol. 300, No. 2, Feb. 1, 1993, pp. 747-750 (6 pages total), CAplus accession No. DN 118:205395.
Ecuador Patent Office; Communication dated Feb. 3, 2018 in application No. IEPI-2018-3879.
Ecuador Patent Office; Communication dated Feb. 3, 2019 in application No. SENADI-2018-53053.
Ecuador Patent Office; Communication dated Feb. 3, 2019 in application No. SENADI-2018-53055.
Elisabeth Gasteiger et al., "ExPASy: the proteomics server for in-depth protein knowledge and analysis", Nucleic Acids Research, 2003, pp. 3784-3788. vol. 31, No. 13, 2003.
International Searching Authority; International Search Report for PCT/KR2016/006984, dated Sep. 12, 2016 (PSA/ISA/210).
International Searching Authority; International Search Report for PCT/KR2017/006922 dated Dec. 7, 2017 (PCT/ISA/210).
International Searching Authority; Written Opinion for PCT/KR2016/006984, dated Sep. 12, 2016 (PCT/ISA/237).
John Eng et al., "Isolation and Characterization of Exendin-4, an Exendin-3 Analogue, from Heloderma suspectum Venom", the Journal of Biological Chemistry, vol. 267, No. 11 Apr. 15, 1992, pp. 7402-7405.
Korean Intellectual Property Office; Communication dated Jul. 12, 2018 in application No. 10-2016-0081976.
United States Patent and Trademark Office; Communication dated Feb. 27, 2019, issued in U.S. Appl. No. 16/023,994.
United States Patent and Trademark Office; Communication dated Jan. 11, 2019, issued in U.S. Appl. No. 16/024,014.
United States Patent and Trademark Office; Communication dated Oct. 31, 2018, issued inU.S. Appl. No. 16/024,014.
Columbia Patent Office; Communication dated Jul 17, 2017 in counterpart application No. NC2017/0006308.
European Patent Office; Communication dated Jun. 12, 2018 in counterpart application No. 15875680.9.
Anonymous, "Calculating approximate isoelectric points for amino acids and peptides", Nov. 1, 2011, pp. 1-2, XP055471990, Retrieved from the Internet: URL:http://www.elcamino.edu/faculty/pdoucette/calculating-approximate-isoelectric-points.pdf (2 pages total).
Korean Application No. 10-2015-0093265 filed on Jun. 30, 2015 with Translation (total 92 pages).
"Endocrine Abstracts", 43rd Annual Meeting of the British Society for Paediatric Endocrinology and Diabetes 2015, Nov. 2015, vol. 39, (total 77 pages).
United States Patent and Trademark Office; Communication dated Jul. 8, 2019, issued in U.S. Appl. No. 16/233,890.
United States Patent and Trademark Office; Communication dated Sep. 9, 2019, issued in U.S. Appl. No. 15/740,668.
Biosynthesis, "N-Terminal Acetylation Amidation Peptides Chemically Synthesized Aminopeptidases Intracellular", Nov. 11, 2008, URL biosyn.com/faq/why-acetylate-and-amidate-a-peptide.aspx (1 page total).
Santoprete et al., "DPP-IV-resistant, long-acting oxyntomodulin derivatives", Journal of Peptide Science, vol. 17, No. 4, Apr. 1, 2011, pp. 270-280, XP055000397.
Cornier et al., "The Metabolic Syndrome", Endocrine Reviews, 2008, vol. 29, No. 7, pp. 777-822 (total 46 pages).
Chabenne et al., "Optimization of the Native Glucagon Sequence for Medicinal Purposes", Journal of Diabetes Science and Technology, vol. 4, Issue 6, Nov. 2010 (10 pages total).
Holz et al., "Glucagon-Like Peptide-1 Synthetic Analogs: New Therapeutic Agents for Use in the Treatment of Diabetes Mellitus", Current Medicinal Chemistry, vol. 10, 2003, pp. 2471-2483.

(56) References Cited

OTHER PUBLICATIONS

Knudsen et al., "Potent Derivatives of Glucagon-like Peptide-1 with Pharmacokinetic Properties Suitable for Once Daily Administration," J. Med. Chem., vol. 43, 2000, pp. 1664-1669.

Lee et al., "PEGylated glucagon-like peptide-1 displays preserved effects on inslin release in isolated pancreatic islets and improved biological activity in db/db mice", Diabetologia, 2006, vol. 49, pp. 1608-1611.

Oka et al., "Endogenous GLP-1 is involved in β-amyloid protein-induced memory impairment and hippocampal neuronal death in rats", Brain Research, 2000, vol. 878, pp. 194-198 (5 pages total).

Suzuki E et al, "A Role of Endogenous GLP-1 in Amnesia and Neuronal Death Induced by Continuous I.C.V. Infusion of Beta-Amyloid Protein in Rat", Japanese Journal of Pharmacology, The Japanese Pharmacological Society, Kyoto, JP, (2000), vol. 82, No. Suppl 1, p. 236P.

\* cited by examiner

SEQUENCE LISTING

```
<160> NUMBER OF SEQ ID NOS: 36

<210> SEQ ID NO 1
<211> LENGTH: 29
<212> TYPE: PRT
<213> ORGANISM: Homo sapiens

<400> SEQUENCE: 1

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr
            20                  25

<210> SEQ ID NO 2
<211> LENGTH: 29
<212> TYPE: PRT
<213> ORGANISM: Artificial Sequence
<220> FEATURE:
<223> OTHER INFORMATION: glucagon derivative

<400> SEQUENCE: 2

His Ser Gln Gly Thr Phe Thr Ser Asp Tyr Ser Lys Tyr Leu Asp Cys
1               5                   10                  15

Asp Arg Ala Gln Asp Phe Val Gln Trp Leu Met Asn Thr
            20                  25

<210> SEQ ID NO 3
<211> LENGTH: 29
<212> TYPE: PRT
<213> ORGANISM: Artificial Sequence
<220> FEATURE:
```

<223> OTHER INFORMATION: glucagon derivative

<400> SEQUENCE: 3

His Ser Gln Gly Thr Phe Thr Ser Asp Tyr Ser Lys Tyr Leu Asp Cys
1               5                   10                  15
Glu Arg Ala Gln Asp Phe Val Gln Trp Leu Met Asn Thr
            20                  25

<210> SEQ ID NO 4
<211> LENGTH: 29
<212> TYPE: PRT
<213> ORGANISM: Artificial Sequence
<220> FEATURE:
<223> OTHER INFORMATION: glucagon derivative

<400> SEQUENCE: 4

His Ser Gln Gly Thr Phe Thr Ser Asp Tyr Ser Lys Tyr Leu Asp Ser
1               5                   10                  15
Cys Asp Ala Gln Asp Phe Val Gln Trp Leu Met Asn Thr
            20                  25

<210> SEQ ID NO 5
<211> LENGTH: 29
<212> TYPE: PRT
<213> ORGANISM: Artificial Sequence
<220> FEATURE:
<223> OTHER INFORMATION: glucagon derivative

<400> SEQUENCE: 5

His Ser Gln Gly Thr Phe Thr Ser Asp Tyr Ser Lys Tyr Leu Asp Ser
1               5                   10                  15
Cys Glu Ala Gln Asp Phe Val Gln Trp Leu Met Asn Thr
            20                  25

<210> SEQ ID NO 6
<211> LENGTH: 29
<212> TYPE: PRT
<213> ORGANISM: Artificial Sequence
<220> FEATURE:
<223> OTHER INFORMATION: glucagon derivative

<400> SEQUENCE: 6

His Ser Gln Gly Thr Phe Thr Ser Asp Tyr Ser Lys Tyr Leu Asp Ser
1               5                   10                  15
Cys Glu Ala Asp Asp Phe Val Gln Trp Leu Met Asn Thr
            20                  25

<210> SEQ ID NO 7
<211> LENGTH: 29
<212> TYPE: PRT
<213> ORGANISM: Artificial Sequence
<220> FEATURE:
<223> OTHER INFORMATION: glucagon derivative

<400> SEQUENCE: 7

Tyr Ser Gln Gly Thr Phe Thr Ser Asp Tyr Ser Lys Tyr Leu Asp Ser
1               5                   10                  15
Cys Glu Ala Asp Asp Phe Val Gln Trp Leu Met Asn Thr
            20                  25

<210> SEQ ID NO 8
<211> LENGTH: 29
<212> TYPE: PRT
<213> ORGANISM: Artificial Sequence

```
<220> FEATURE:
<223> OTHER INFORMATION: glucagon derivative
<220> FEATURE:
<221> NAME/KEY: VARIANT
<222> LOCATION: (2)
<223> OTHER INFORMATION: Xaa is aminoisobutyric acid

<400> SEQUENCE: 8

Tyr Xaa Gln Gly Thr Phe Thr Ser Asp Tyr Ser Lys Tyr Leu Asp Ser
1               5                   10                  15

Cys Asp Ala Gln Asp Phe Val Gln Trp Leu Ile Asn Thr
            20                  25

<210> SEQ ID NO 9
<211> LENGTH: 29
<212> TYPE: PRT
<213> ORGANISM: Artificial Sequence
<220> FEATURE:
<223> OTHER INFORMATION: glucagon derivative
<220> FEATURE:
<221> NAME/KEY: VARIANT
<222> LOCATION: (2)
<223> OTHER INFORMATION: Xaa is aminoisobutyric acid

<400> SEQUENCE: 9

Tyr Xaa Gln Gly Thr Phe Thr Ser Asp Tyr Ser Lys Tyr Leu Asp Ser
1               5                   10                  15

Cys Asp Ala Gln Asp Phe Val Val Trp Leu Ile Asn Thr
            20                  25

<210> SEQ ID NO 10
<211> LENGTH: 29
<212> TYPE: PRT
<213> ORGANISM: Artificial Sequence
<220> FEATURE:
<223> OTHER INFORMATION: glucagon derivative
<220> FEATURE:
<221> NAME/KEY: VARIANT
<222> LOCATION: (2)
<223> OTHER INFORMATION: Xaa is aminoisobutyric acid

<400> SEQUENCE: 10

Tyr Xaa Gln Gly Thr Phe Thr Ser Asp Tyr Ser Lys Tyr Leu Asp Ser
1               5                   10                  15

Cys Asp Ala Asp Asp Phe Val Val Trp Leu Ile Asn Thr
            20                  25

<210> SEQ ID NO 11
<211> LENGTH: 29
<212> TYPE: PRT
<213> ORGANISM: Artificial Sequence
<220> FEATURE:
<223> OTHER INFORMATION: glucagon derivative
<220> FEATURE:
<221> NAME/KEY: VARIANT
<222> LOCATION: (2)
<223> OTHER INFORMATION: Xaa is aminoisobutyric acid

<400> SEQUENCE: 11

Tyr Xaa Gln Gly Thr Phe Thr Ser Asp Tyr Ser Lys Tyr Leu Asp Glu
1               5                   10                  15

Lys Cys Ala Lys Glu Phe Val Gln Trp Leu Met Asn Thr
            20                  25

<210> SEQ ID NO 12
<211> LENGTH: 29
<212> TYPE: PRT
```

<213> ORGANISM: Artificial Sequence
<220> FEATURE:
<223> OTHER INFORMATION: glucagon derivative
<220> FEATURE:
<221> NAME/KEY: VARIANT
<222> LOCATION: (2)
<223> OTHER INFORMATION: Xaa is aminoisobutyric acid

<400> SEQUENCE: 12

Tyr Xaa Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr
            20                  25

<210> SEQ ID NO 13
<211> LENGTH: 29
<212> TYPE: PRT
<213> ORGANISM: Artificial Sequence
<220> FEATURE:
<223> OTHER INFORMATION: glucagon derivative
<220> FEATURE:
<221> NAME/KEY: VARIANT
<222> LOCATION: (2)
<223> OTHER INFORMATION: Xaa is aminoisobutyric acid

<400> SEQUENCE: 13

Tyr Xaa Gln Gly Thr Phe Thr Ser Asp Tyr Ser Cys Tyr Leu Asp Glu
1               5                   10                  15

Lys Arg Ala Lys Glu Phe Val Gln Trp Leu Met Asn Thr
            20                  25

<210> SEQ ID NO 14
<211> LENGTH: 29
<212> TYPE: PRT
<213> ORGANISM: Artificial Sequence
<220> FEATURE:
<223> OTHER INFORMATION: glucagon derivative
<220> FEATURE:
<221> NAME/KEY: VARIANT
<222> LOCATION: (2)
<223> OTHER INFORMATION: Xaa is aminoisobutyric acid

<400> SEQUENCE: 14

Tyr Xaa Gln Gly Thr Phe Thr Ser Asp Tyr Ser Lys Tyr Leu Asp Cys
1               5                   10                  15

Lys Arg Ala Lys Glu Phe Val Gln Trp Leu Met Asn Thr
            20                  25

<210> SEQ ID NO 15
<211> LENGTH: 29
<212> TYPE: PRT
<213> ORGANISM: Artificial Sequence
<220> FEATURE:
<223> OTHER INFORMATION: glucagon derivative
<220> FEATURE:
<221> NAME/KEY: VARIANT
<222> LOCATION: (2)
<223> OTHER INFORMATION: Xaa is aminoisobutyric acid

<400> SEQUENCE: 15

Tyr Xaa Gln Gly Thr Phe Thr Ser Asp Tyr Ser Lys Tyr Leu Cys Glu
1               5                   10                  15

Lys Arg Ala Gln Asp Phe Val Val Trp Leu Met Asn Thr
            20                  25

<210> SEQ ID NO 16
<211> LENGTH: 29

```
<212> TYPE: PRT
<213> ORGANISM: Artificial Sequence
<220> FEATURE:
<223> OTHER INFORMATION: glucagon derivative
<220> FEATURE:
<221> NAME/KEY: VARIANT
<222> LOCATION: (2)
<223> OTHER INFORMATION: Xaa is aminoisobutyric acid

<400> SEQUENCE: 16

Tyr Xaa Gln Gly Thr Phe Thr Ser Asp Tyr Ser Lys Tyr Leu Asp Cys
1               5                   10                  15

Arg Arg Ala Gln Val Phe Val Gln Trp Leu Met Arg Thr
            20                  25

<210> SEQ ID NO 17
<211> LENGTH: 29
<212> TYPE: PRT
<213> ORGANISM: Artificial Sequence
<220> FEATURE:
<223> OTHER INFORMATION: glucagon derivative
<220> FEATURE:
<221> NAME/KEY: VARIANT
<222> LOCATION: (2)
<223> OTHER INFORMATION: Xaa is aminoisobutyric acid

<400> SEQUENCE: 17

Tyr Xaa Gln Gly Thr Phe Thr Ser Asp Tyr Ser Lys Tyr Leu Asp Cys
1               5                   10                  15

Val Arg Ala Gln Asp Phe Val Gln Trp Leu Met Arg Thr
            20                  25

<210> SEQ ID NO 18
<211> LENGTH: 29
<212> TYPE: PRT
<213> ORGANISM: Artificial Sequence
<220> FEATURE:
<223> OTHER INFORMATION: glucagon derivative
<220> FEATURE:
<221> NAME/KEY: VARIANT
<222> LOCATION: (2)
<223> OTHER INFORMATION: Xaa is aminoisobutyric acid

<400> SEQUENCE: 18

Tyr Xaa Gln Gly Thr Phe Thr Ser Asp Tyr Ser Lys Tyr Leu Asp Ser
1               5                   10                  15

Arg Arg Ala Cys Asp Phe Arg Leu Trp Leu Met Asn Thr
            20                  25

<210> SEQ ID NO 19
<211> LENGTH: 29
<212> TYPE: PRT
<213> ORGANISM: Artificial Sequence
<220> FEATURE:
<223> OTHER INFORMATION: glucagon derivative
<220> FEATURE:
<221> NAME/KEY: VARIANT
<222> LOCATION: (2)
<223> OTHER INFORMATION: Xaa is aminoisobutyric acid
<220> FEATURE:
<221> NAME/KEY: VARIANT
<222> LOCATION: (16), (20)
<223> OTHER INFORMATION: amino acids at position 16 and position 20 form
      a ring

<400> SEQUENCE: 19

Tyr Xaa Gln Gly Thr Phe Thr Ser Asp Tyr Ser Lys Tyr Leu Cys Glu
1               5                   10                  15
```

Lys Arg Ala Lys Glu Phe Val Gln Trp Leu Met Asn Thr
            20                  25

<210> SEQ ID NO 20
<211> LENGTH: 29
<212> TYPE: PRT
<213> ORGANISM: Artificial Sequence
<220> FEATURE:
<223> OTHER INFORMATION: glucagon derivative
<220> FEATURE:
<221> NAME/KEY: VARIANT
<222> LOCATION: (2)
<223> OTHER INFORMATION: Xaa is aminoisobutyric acid
<220> FEATURE:
<221> NAME/KEY: VARIANT
<222> LOCATION: (16), (20)
<223> OTHER INFORMATION: amino acids at position 16 and position 20 form
      a ring

<400> SEQUENCE: 20

Tyr Xaa Gln Gly Thr Phe Thr Ser Asp Tyr Ser Lys Tyr Leu Asp Glu
1               5                   10                  15

Cys Arg Ala Lys Glu Phe Val Gln Trp Leu Met Asn Thr
            20                  25

<210> SEQ ID NO 21
<211> LENGTH: 29
<212> TYPE: PRT
<213> ORGANISM: Artificial Sequence
<220> FEATURE:
<223> OTHER INFORMATION: glucagon derivative
<220> FEATURE:
<221> NAME/KEY: VARIANT
<222> LOCATION: (2)
<223> OTHER INFORMATION: Xaa is aminoisobutyric acid
<220> FEATURE:
<221> NAME/KEY: VARIANT
<222> LOCATION: (16), (20)
<223> OTHER INFORMATION: amino acids at position 16 and position 20 form
      a ring

<400> SEQUENCE: 21

Tyr Xaa Gln Gly Thr Phe Thr Ser Asp Tyr Ser Lys Tyr Leu Asp Glu
1               5                   10                  15

Lys Cys Ala Lys Glu Phe Val Gln Trp Leu Met Asn Thr
            20                  25

<210> SEQ ID NO 22
<211> LENGTH: 29
<212> TYPE: PRT
<213> ORGANISM: Artificial Sequence
<220> FEATURE:
<223> OTHER INFORMATION: glucagon derivative
<220> FEATURE:
<221> NAME/KEY: VARIANT
<222> LOCATION: (2)
<223> OTHER INFORMATION: Xaa is aminoisobutyric acid
<220> FEATURE:
<221> NAME/KEY: VARIANT
<222> LOCATION: (16), (20)
<223> OTHER INFORMATION: amino acids at position 16 and position 20 form
      a ring

<400> SEQUENCE: 22

Tyr Xaa Gln Gly Thr Phe Thr Ser Asp Tyr Ser Lys Tyr Leu Asp Glu
1               5                   10                  15

Lys Arg Cys Lys Glu Phe Val Gln Trp Leu Met Asn Thr
            20                  25

```
<210> SEQ ID NO 23
<211> LENGTH: 29
<212> TYPE: PRT
<213> ORGANISM: Artificial Sequence
<220> FEATURE:
<223> OTHER INFORMATION: glucagon derivative
<220> FEATURE:
<221> NAME/KEY: VARIANT
<222> LOCATION: (2)
<223> OTHER INFORMATION: Xaa is aminoisobutyric acid
<220> FEATURE:
<221> NAME/KEY: VARIANT
<222> LOCATION: (16), (20)
<223> OTHER INFORMATION: amino acids at position 16 and position 20 form
      a ring

<400> SEQUENCE: 23

Tyr Xaa Gln Gly Thr Phe Thr Ser Asp Tyr Ser Lys Tyr Cys Asp Glu
1               5                   10                  15

Lys Arg Ala Lys Glu Phe Val Gln Trp Leu Met Asn Thr
            20                  25

<210> SEQ ID NO 24
<211> LENGTH: 29
<212> TYPE: PRT
<213> ORGANISM: Artificial Sequence
<220> FEATURE:
<223> OTHER INFORMATION: glucagon derivative
<220> FEATURE:
<221> NAME/KEY: VARIANT
<222> LOCATION: (2)
<223> OTHER INFORMATION: Xaa is aminoisobutyric acid
<220> FEATURE:
<221> NAME/KEY: VARIANT
<222> LOCATION: (16), (20)
<223> OTHER INFORMATION: amino acids at position 16 and position 20 form
      a ring

<400> SEQUENCE: 24

Tyr Xaa Gln Gly Thr Phe Thr Ser Asp Tyr Ser Lys Cys Leu Asp Glu
1               5                   10                  15

Lys Arg Ala Lys Glu Phe Val Gln Trp Leu Met Asn Thr
            20                  25

<210> SEQ ID NO 25
<211> LENGTH: 29
<212> TYPE: PRT
<213> ORGANISM: Artificial Sequence
<220> FEATURE:
<223> OTHER INFORMATION: glucagon derivative
<220> FEATURE:
<221> NAME/KEY: VARIANT
<222> LOCATION: (2)
<223> OTHER INFORMATION: Xaa is aminoisobutyric acid
<220> FEATURE:
<221> NAME/KEY: VARIANT
<222> LOCATION: (16), (20)
<223> OTHER INFORMATION: amino acids at position 16 and position 20 form
      a ring

<400> SEQUENCE: 25

Tyr Xaa Gln Gly Thr Phe Thr Ser Asp Tyr Ser Lys Tyr Leu Asp Glu
1               5                   10                  15

Lys Arg Ala Lys Cys Phe Val Gln Trp Leu Met Asn Thr
            20                  25

<210> SEQ ID NO 26
<211> LENGTH: 29
<212> TYPE: PRT
<213> ORGANISM: Artificial Sequence
```

```
<220> FEATURE:
<223> OTHER INFORMATION: glucagon derivative
<220> FEATURE:
<221> NAME/KEY: VARIANT
<222> LOCATION: (2)
<223> OTHER INFORMATION: Xaa is aminoisobutyric acid
<220> FEATURE:
<221> NAME/KEY: VARIANT
<222> LOCATION: (16), (20)
<223> OTHER INFORMATION: amino acids at position 16 and position 20 form
      a ring

<400> SEQUENCE: 26

Trp Xaa Gln Gly Thr Phe Thr Ser Asp Tyr Ser Lys Tyr Leu Asp Glu
1               5                   10                  15

Cys Arg Ala Lys Asp Phe Val Gln Trp Leu Met Asn Thr
            20                  25

<210> SEQ ID NO 27
<211> LENGTH: 29
<212> TYPE: PRT
<213> ORGANISM: Artificial Sequence
<220> FEATURE:
<223> OTHER INFORMATION: glucagon derivative
<220> FEATURE:
<221> NAME/KEY: VARIANT
<222> LOCATION: (2)
<223> OTHER INFORMATION: Xaa is aminoisobutyric acid
<220> FEATURE:
<221> NAME/KEY: VARIANT
<222> LOCATION: (16), (20)
<223> OTHER INFORMATION: amino acids at position 16 and position 20 form
      a ring

<400> SEQUENCE: 27

Tyr Xaa Gln Gly Thr Phe Val Ser Asp Tyr Ser Lys Tyr Leu Asp Glu
1               5                   10                  15

Cys Arg Ala Lys Asp Phe Val Gln Trp Leu Met Asn Thr
            20                  25

<210> SEQ ID NO 28
<211> LENGTH: 29
<212> TYPE: PRT
<213> ORGANISM: Artificial Sequence
<220> FEATURE:
<223> OTHER INFORMATION: glucagon derivative
<220> FEATURE:
<221> NAME/KEY: VARIANT
<222> LOCATION: (2)
<223> OTHER INFORMATION: Xaa is aminoisobutyric acid
<220> FEATURE:
<221> NAME/KEY: VARIANT
<222> LOCATION: (16), (20)
<223> OTHER INFORMATION: amino acids at position 16 and position 20 form
      a ring

<400> SEQUENCE: 28

Trp Xaa Gln Gly Thr Phe Val Ser Asp Tyr Ser Lys Tyr Leu Asp Glu
1               5                   10                  15

Cys Arg Ala Lys Asp Phe Val Gln Trp Leu Met Asn Thr
            20                  25

<210> SEQ ID NO 29
<211> LENGTH: 29
<212> TYPE: PRT
<213> ORGANISM: Artificial Sequence
<220> FEATURE:
<223> OTHER INFORMATION: glucagon derivative
<220> FEATURE:
<221> NAME/KEY: VARIANT
```

```
<222> LOCATION: (2)
<223> OTHER INFORMATION: Xaa is aminoisobutyric acid
<220> FEATURE:
<221> NAME/KEY: VARIANT
<222> LOCATION: (16), (20)
<223> OTHER INFORMATION: amino acids at position 16 and position 20 form
      a ring

<400> SEQUENCE: 29

Tyr Xaa Gln Gly Thr Phe Thr Ser Asp Tyr Ser Lys Cys Leu Asp Glu
1               5                   10                  15

Arg Arg Ala Lys Asp Phe Val Gln Trp Leu Met Asn Thr
            20                  25

<210> SEQ ID NO 30
<211> LENGTH: 29
<212> TYPE: PRT
<213> ORGANISM: Artificial Sequence
<220> FEATURE:
<223> OTHER INFORMATION: glucagon derivative
<220> FEATURE:
<221> NAME/KEY: VARIANT
<222> LOCATION: (2)
<223> OTHER INFORMATION: Xaa is aminoisobutyric acid
<220> FEATURE:
<221> NAME/KEY: VARIANT
<222> LOCATION: (16), (20)
<223> OTHER INFORMATION: amino acids at position 16 and position 20 form
      a ring

<400> SEQUENCE: 30

Trp Xaa Gln Gly Thr Phe Thr Ser Asp Tyr Ser Lys Cys Leu Asp Glu
1               5                   10                  15

Arg Arg Ala Glu Asp Phe Val Gln Trp Leu Met Asn Thr
            20                  25

<210> SEQ ID NO 31
<211> LENGTH: 29
<212> TYPE: PRT
<213> ORGANISM: Artificial Sequence
<220> FEATURE:
<223> OTHER INFORMATION: glucagon derivative
<220> FEATURE:
<221> NAME/KEY: VARIANT
<222> LOCATION: (2)
<223> OTHER INFORMATION: Xaa is aminoisobutyric acid
<220> FEATURE:
<221> NAME/KEY: VARIANT
<222> LOCATION: (17), (21)
<223> OTHER INFORMATION: amino acids at position 17 and position 21 form
      a ring

<400> SEQUENCE: 31

Tyr Xaa Gln Gly Thr Phe Thr Ser Asp Tyr Ser Lys Tyr Leu Asp Cys
1               5                   10                  15

Lys Arg Ala Lys Glu Phe Val Gln Trp Leu Met Asn Thr
            20                  25

<210> SEQ ID NO 32
<211> LENGTH: 28
<212> TYPE: PRT
<213> ORGANISM: Artificial Sequence
<220> FEATURE:
<223> OTHER INFORMATION: glucagon derivative
<220> FEATURE:
<221> NAME/KEY: VARIANT
<222> LOCATION: (15), (19)
<223> OTHER INFORMATION: amino acids at position 15 and position 19 form
      a ring
```

<400> SEQUENCE: 32

Ser Gln Gly Thr Phe Thr Ser Asp Tyr Ser Lys Tyr Leu Asp Glu Cys
 1               5                  10                  15

Arg Ala Lys Glu Phe Val Gln Trp Leu Met Asn Thr
            20                  25

<210> SEQ ID NO 33
<211> LENGTH: 29
<212> TYPE: PRT
<213> ORGANISM: Artificial Sequence
<220> FEATURE:
<223> OTHER INFORMATION: glucagon derivative
<220> FEATURE:
<221> NAME/KEY: VARIANT
<222> LOCATION: (2)
<223> OTHER INFORMATION: Xaa is aminoisobutyric acid
<220> FEATURE:
<221> NAME/KEY: VARIANT
<222> LOCATION: (16), (20)
<223> OTHER INFORMATION: amino acids at position 16 and position 20 form
      a ring

<400> SEQUENCE: 33

Trp Xaa Gln Gly Thr Phe Thr Ser Asp Tyr Ser Lys Tyr Cys Asp Glu
 1               5                  10                  15

Arg Arg Ala Lys Glu Phe Val Gln Trp Leu Met Asn Thr
            20                  25

<210> SEQ ID NO 34
<211> LENGTH: 29
<212> TYPE: PRT
<213> ORGANISM: Artificial Sequence
<220> FEATURE:
<223> OTHER INFORMATION: glucagon derivative
<220> FEATURE:
<221> NAME/KEY: VARIANT
<222> LOCATION: (2)
<223> OTHER INFORMATION: Xaa is aminoisobutyric acid
<220> FEATURE:
<221> NAME/KEY: VARIANT
<222> LOCATION: (16), (20)
<223> OTHER INFORMATION: amino acids at position 16 and position 20 form
      a ring

<400> SEQUENCE: 34

Tyr Xaa Gln Gly Thr Phe Thr Ser Asp Tyr Ser Lys Tyr Cys Asp Glu
 1               5                  10                  15

Arg Arg Ala Lys Glu Phe Val Gln Trp Leu Met Asn Thr
            20                  25

<210> SEQ ID NO 35
<211> LENGTH: 34
<212> TYPE: DNA
<213> ORGANISM: Artificial Sequence
<220> FEATURE:
<223> OTHER INFORMATION: forward primer

<400> SEQUENCE: 35
cagcgacacc gaccgtcccc ccgtacttaa ggcc                            34

<210> SEQ ID NO 36
<211> LENGTH: 32
<212> TYPE: DNA
<213> ORGANISM: Artificial Sequence
<220> FEATURE:

```
<223> OTHER INFORMATION: reverse primer

<400> SEQUENCE: 36
ctaaccgact ctcggggaag actgagctcg cc                                          32
```

GLUCAGON DERIVATIVES WITH IMPROVED STABILITY

CROSS REFERENCE TO RELATED APPLICATIONS

This application is a National Stage of International Application No. PCT/KR2015/014422 filed Dec. 30, 2015, claiming priority based on Korean Patent Application No. 10-2014-0193800 filed Dec. 30, 2014, the contents of all of which are incorporated herein by reference in their entirety.

TECHNICAL FIELD

The present invention relates to novel glucagon derivatives having improved physical properties due to the change in isoelectric point (pI), and a composition for preventing or treating hypoglycemia and obesity containing the same as an active ingredient.

BACKGROUND ART

Recent economic advances and lifestyle changes have been accompanied by great changes in dietary habits. Particularly, busy people of today are overweight and obese due to high-calorie diets and insufficient exercise. The World Health Organization (WHO) has reported that more than one billion adults are overweight worldwide, among them over three million are clinically diagnosed with severe obesity, and 25,000 people die of overweight- or obesity-related diseases every year (World Health Organization, Global Strategy on Diet, Physical Activity and Health, 2004).

Overweight and obesity are responsible for increasing blood pressure and cholesterol levels and causing or worsening various diseases, such as cardiac diseases, diabetes, arthritis, etc. In addition, the problem of obesity is also becoming a major cause in the increased incidence of atherosclerosis, hypertension, hyperlipidemia, or heart diseases in children or teenagers as well as in adults. However, obesity is not easy to treat, because it is a complex disease associated with the mechanisms of appetite control and energy metabolism. Accordingly, the treatment of obesity requires not only the patient's own efforts, but also a method capable of treating abnormal mechanisms associated with appetite control and energy metabolism. Thus, efforts have been made to develop drugs for treating the abnormal mechanisms.

As a result of these efforts, drugs such as Rimonabant (Sanofi-Aventis), Sibutramin (Abbott), Contrave (Takeda), and Orlistat (Roche) have been developed, but they have the disadvantages of serious adverse effects or very weak anti-obesity effects. For example, according to reports, Rimonabant showed a side-effect of central nervous system disorder, Sibutramine and Contrave showed cardiovascular side-effects, and Orlistat showed only about 4 kg of weight loss when taken for 1 year. Accordingly, there have been no therapeutic agents for obesity which can be prescribed safely for obese patients.

Many extensive studies have been made to develop novel therapeutic agents for obesity which can resolve the problems of the conventional anti-obesity drugs. Recently, glucagon derivatives have received much attention. Glucagon is produced by the pancreas when blood glucose levels drop as a result of other medications or diseases, or hormone or enzyme deficiencies. Glucagon stimulates glycogen breakdown in the liver, and facilitates glucose release to raise blood glucose levels to a normal range. In addition to the effect of increasing the blood glucose levels, glucagon suppresses appetite and activates hormone-sensitive lipase of adipocytes to facilitate lipolysis, thereby showing an anti-obesity effect. However, the use of glucagon as a therapeutic agent has been limited due to its low solubility and its property of being precipitated at a neutral pH.

One of the glucagon derivatives, glucagon like peptide-1 (GLP-1), is under development as a therapeutic agent for treating hyperglycemia in patients with diabetes. GLP-1 has the functions of stimulating insulin synthesis and secretion, inhibiting glucagon secretion, slowing gastric emptying, increasing glucose utilization, and inhibiting food intake.

Exendin-4, prepared from lizard venom and having an amino acid homology of about 50% with GLP-1, was also reported to activate the GLP-1 receptor, thereby reducing hyperglycemia in patients with diabetes. However, anti-obesity drugs containing GLP-1 are reported to show side-effects such as vomiting and nausea.

As an alternative to GLP-1, therefore, much attention has been focused on oxyntomodulin, which can bind to both receptors of the two peptides. GLP-1 and glucagon. Oxyntomodulin is a peptide prepared from a glucagon precursor, pre-glucagon, and has the functions of inhibiting food intake and enhancing satiety of GLP-1, and has lipolytic activity like glucagon, thus increasing its potency in anti-obesity therapy.

However, oxyntomodulin or derivatives thereof have a serious drawback in that an excess amount of the drug should be administered daily for obesity treatment because they have low efficacy and a short in vivo half-life.

Additionally, when both activities of GLP-1 and glucagon are present in a single peptide, the activity ratio thereof becomes fixed, and thus it is difficult to use a dual agonist with various ratios. Accordingly, a combined therapy capable of using various activity ratios by adjusting the contents of GLP-1 and glucagon may be more effective.

However, for the combined therapy, it is required to improve the physical characteristics of glucagon, which aggregates at a neutral pH and precipitates with time, thus showing poor solubility.

Under these circumstances, the present inventors have developed glucagon derivatives with partial modifications of the amino acid sequence of glucagon for the improvement of the therapeutic effects of glucagon on hypoglycemia and obesity by improving the physical properties of glucagon, and have discovered that these glucagon derivatives have improved solubility and higher stability at a neutral pH, thereby completing the present invention.

DISCLOSURE

Technical Problem

An object of the present invention is to provide a novel glucagon derivative with improved physical properties.

Another object of the present invention is to provide a composition for preventing or treating hypoglycemia containing the glucagon derivative as an active ingredient.

A further object of the present invention is to provide a composition for preventing or treating obesity containing the glucagon derivative as an active ingredient.

Technical Solution

In order to achieve the above objects, in an aspect, the present invention provides a novel glucagon derivative which includes the amino acid sequence of the following General Formula 1 and has an isoelectric point (pI), which is not the same as, i.e., different from, that of native glucagon:

(General Formula 1)
X1-X2-QGTF-X7-SDYS-X12-X13-X14-X15-X16-X17-X18-
X19-X20-X21-F-X23-X24-W-L-X27-X28-T wherein, in General Formula 1, X1 is histidine, desamino-histidine, N-dimethyl-histidine, β-hydroxyimidazopropionic acid, 4-imidazoacetic acid, β-carboxyimidazopropionic acid, tryptophan, tyrosine, or deleted;

X2 is α-methyl-glutamic acid, aininoisobutyric acid (Aib), D-alanine, glycine, Sar(N-methylglycine), serine, or D-serine;

X7 is threonine or valine;

X12 is lysine or cysteine;

X13 is tyrosine or cysteine;

X14 is leucine or cysteine;

X15 is aspartic acid, glutamic acid, or cysteine;

X16 is glutamic acid, aspartic acid, serine, α-methyl-glutamic acid, or cysteine;

X17 is aspartic acid, glutamine, glutamic acid, lysine, arginine, serine, valine, or cysteine;

X18 is aspartic acid, glutamine, glutamic acid, arginine, or cysteine;

X19 is alanine or cysteine;

X20 is lysine, glutamic acid, glutamine, aspartic acid, lysine, or cysteine;

X21 is aspartic acid, glutamic acid, valine, or cysteine;

X23 is valine or arginine;

X24 is valine, leucine, glutamine, or arginine;

X27 is isoleucine or methionine; and

X28 is arginine or asparagine (with the proviso that when the amino acid sequence of General Formula 1 is identical to SEQ ID NO: 1, it is excluded).

The glucagon derivative according to the present invention includes a peptide, a peptide derivative, or a peptide mimetic, which has improved physical properties by having a different pI from that of native glucagon by modifying a part of the amino acid(s) of native glucagon.

As used herein, the term "native glucagon" refers to native human glucagon having the sequence of (SEQ ID NO: 1)
His-Ser-Gln-Gly-Thr-Phe-Thr-Ser-Asp-Tyr-Ser-Lys-
Tyr-Leu-Asp-Ser-Arg-Arg-Ala-Gln-Asp-Phe-Val-Gln-
Trp-Leu-Met-Asn-Thr.

Referring to the sequence of General Formula I according to the present invention, the amino acids proceed from the N-terminus on the left to the C-terminus on the right according to the conventional method of description. Accordingly, when the "position" of any particular residue is referred to in the sequence of General Formula 1, it should be interpreted in the same manner as when any position in native glucagon or other molecules is referred to.

Over the entire specification of the present invention, not only the conventional one-letter or three-letter codes for naturally occurring amino acids, but also those three-letter codes generally allowed for other amino acids, such as α-aminoisobutyric acid (Aib), Sar(N-methylglycine), and α-methyl-glutamic acid, are used.

Additionally, the amino acids mentioned herein are abbreviated according to the nomenclature rules of IUPAC-IUB as follows:

| | | | |
|---|---|---|---|
| Alanine | A; | Arginine | R; |
| Asparagine | N; | Aspartic acid | D; |
| Cysteine | C; | Glutamic acid | E; |
| Glutamine | Q; | Glycine | G; |
| Histidine | H; | Isoleucine | I; |
| Leucine | L; | Lysine | K; |
| Methionine | M; | Phenylalanine | F; |
| Proline | P; | Serine | S; |
| Threonine | T; | Tryptophan | W; |
| Tyrosine | Y; and | Valine | V. |

As used herein, the term "peptide" refers to a compound of two or more native and non-native amino acids or amino acid derivatives such as α-amino acids linked by a peptide bond. As used herein, the term "glucagon derivative" refers to a peptide including the sequence of General Formula 1 or a derivative thereof, an analog, or a modified product thereof. The peptide according to the present invention includes peptidomimetics, which have a change in pI compared to that of native glucagon by modifying a part of the amino acid(s) of glucagon in the form of a substitution, etc. In an exemplary embodiment of the present invention, the glucagon derivative has an isoelectric point different from that of native glucagon while maintaining the activity of a glucagon receptor. In a more specific exemplary embodiment of the present invention, the glucagon derivative refers to a peptide with improved solubility of native glucagon at a physiological pH while maintaining the glucagon receptor activity.

As used herein, the term "pI" or "isoelectric point" refers to the pH value at which a macromolecule such as a polypeptide has no net charge (0). In the case of a polypeptide with various charged functional groups, the net charge of the total polypeptide is "0" at a point where the pH value is the same as that of pI. The net charge of the polypeptide at a pH higher than the pI will be negative while the net charge of the polypeptide at a pH lower than the pI will be positive.

The pI values may be measured or estimated by a conventional method used in the art. For example, the pI values may be measured on an immobilized pH gradient gel consisting of polyacrylamide, starch, or agarose by isoelectric electrophoresis, or, for example, may be estimated from an amino acid sequence using a pI/MW tool (expasy.org/tools/pi_tool.html; Gasteiger et al., 2003) in an ExPASy server.

In a specific embodiment of the present invention, the glucagon derivative containing an amino acid sequence of General Formula I encompasses any peptide that is prepared by the substitution, addition, deletion, or post-translational modification (e.g., methylation, acylation, ubiquitination, or intramolecular covalent bonding) of amino acid(s) in the amino acid sequence of native glucagon represented by SEQ ID NO: 1, which exhibits improved solubility according to the pH of a solution due to the difference of its pI from that of native glucagon while maintaining the glucagon receptor activities as they are, thereby having improved in vivo chemical stability.

During the substitution or addition of amino acids, not only the 20 amino acids commonly found in human proteins, but also atypical or non-naturally occurring amino acids and derivatives thereof can be used. Commercial sources of atypical amino acids may include Sigma-Aldrich, ChemPep Inc., Genzyme Pharmaceuticals, etc. The peptides including these amino acids and atypical peptide sequences may be synthesized and purchased from commercial suppliers, e.g., American Peptide Company, Bachem (USA), or Anygen (Korea). Amino acid derivatives, e.g., desamino-histidine, β-hydroxyimidazopropionic acid, 4-imidazoacetic acid, or β-carboxyimidazopropionic acid, may be obtained in the same manner.

Since glucagon has a pH of about 7, it is insoluble in a solution having a pH of 6 to 8 and tends to precipitate at a neutral pH. In an aqueous solution with a pH of 3 or below, glucagon is dissolved at the initial stage but precipitates within one hour by forming a gel. Since the gelated glucagon mainly consists of β-sheet fibrils, the administration of the thus-precipitated glucagon via an injection needle or intravenous injection will block blood vessels, and thus is not suitable for use as an injection agent. In order to delay the precipitation process, acidic (pH of 2 to 4) formulations are commonly used, and by doing so, glucagon can be maintained in a relatively non-aggregated state for a short period of time. However, glucagon can form fibrils very rapidly at a low pH, and thus these acidic formulations must be injected upon preparation.

It is widely known in the art that the solubility, activity, and stability of a protein in a solution can vary according to pI (Shaw, K. L. et al., Protein Science 10, pp 1206-1215, 2001).

As such, the present inventors have developed glucagon derivatives with extended stability and functional effects by modifying the sequence of native glucagon, thereby altering its pI. The glucagon derivatives of the present invention, by having an altered pI compared to that of native glucagon, are characterized in that they have improved solubility and stability according to the pH of a given solution, compared to that of native glucagon.

In a specific embodiment of the present invention, the glucagon derivative may be a peptide in which, in the amino acid sequence of General Formula I, X1 is histidine or tryptophan, tyrosine, or deleted;
X2 is serine or aminoisobutyric acid (Aib);
X7 is threonine or valine;
X12 is lysine or cysteine;
X13 is tyrosine or cysteine;
X14 is leucine or cysteine;
X15 is aspartic acid or cysteine;
X16 is glutamic acid, aspartic acid, serine, or cysteine;
X17 is aspartic acid, glutamic acid, lysine, arginine, valine, or cysteine;
X18 is aspartic acid, glutamic acid, arginine, or cysteine;
X19 is alanine or cysteine;
X20 is lysine, glutamic acid, glutamine, aspartic acid, lysine, or cysteine;
X21 is aspartic acid, glutamic acid, valine, or cysteine;
X23 is valine or arginine;
X24 is valine, leucine, or glutamine;
X27 is isoleucine or methionine; and
X28 is arginine or asparagine (with the proviso that when the amino acid sequence of General Formula 1 is identical to SEQ ID NO: 1, it is excluded).

More preferably, the glucagon derivative of the present invention may be a peptide including any one amino acid sequence among the amino acid sequences represented by SEQ ID NOS: 2 to 34.

The peptide including the glucagon derivative of the present invention may be prepared by a standard synthesis method, a recombinant expression system, or any other method in the art. Accordingly, the glucagon analog according to the present invention may be synthesized by many methods including the methods described below:

(a) a method of synthesizing a peptide by a solid-phase or liquid-phase method stepwise or by fragment assembly, followed by isolation and purification of the final peptide product; or (b) a method of expressing a nucleic acid construct encoding a peptide in a host cell and recovering the expression product from the host cell culture; or (c) a method of performing an in vitro cell-free expression of a nucleic acid construct encoding a peptide and recovering the expression product therefrom; or (d) a method of obtaining peptide fragments by any combination of the methods (a), (b), and (c), obtaining the peptide by linking the peptide fragments, and then recovering the peptide.

In an exemplary aspect of the present invention, it was confirmed that the glucagon derivative of the present invention has a different pI compared to that of native glucagon (see Table 1). As a result, the glucagon derivative of the present invention has improved solubility and higher stability according to the pH of a given solution, compared to that of native glucagon. Accordingly, the glucagon derivative of the present invention can increase patient compliance when used as a hypoglycemic agent and is also suitable for the combined administration to be administered in combination with other anti-obesity agents, and thus can be effectively used for the prevention and treatment of hypoglycemia and obesity.

In this regard, the glucagon derivative of the present invention can provide an attractive therapeutic selection regarding hypoglycemia, obesity, or associated diseases thereof.

For example, the glucagon derivative of the present invention is a major insulin response-controlling hormone, and can be effectively used for the treatment of severe hypoglycemia in diabetic patients.

Additionally, the glucagon derivative of the present invention may be used as a pharmaceutical drug not only for preventing body weight increase, promotion of body weight decrease, reduction of overweight, and obesities including morbid obesity(e.g., by controlling appetite, ingestion, food intake, calorie intake, and/or energy consumption), but also for treating obesity-related inflammation, obesity-related gallbladder disease, and obesity-induced sleep apnea, but is not limited thereto, and may be used for treating the associated diseases or health conditions thereof. The glucagon derivative of the present invention may also be used for treating the health conditions that may be associated with obesity, such as metabolic syndrome, hypertension, atherosclerosis-induced dyslipidemia, arteriosclerosis, arterial chlerosis, coronary heart disease, strokes, etc. However, the effects of the glucagon derivative according to the present invention may be mediated entirely or partially by the body weight-related effects described above or may be independent of the same.

Meanwhile, for the improvement of the therapeutic effects of the glucagon derivative of the present invention, the glucagon derivative may be modified using the typical techniques in the art, including a modification with polymers such as polyethylene glycol (PEG) and sugar chains, or a fusion with albumin, transferrin, fatty acid, and immunoglobulin, etc. For example, at least one amino acid side chain within the compounds of the present invention may be attached to a polymer in order to increase in vivo solubility and/or half-lives, and/or increase bioavailabilities thereof.

These modifications are known to reduce the clearance of therapeutic proteins and peptides.

For these polymers, soluble (amphipathic or hydrophilic), non-toxic, and pharmaceutically inert polymers are appropriate, and preferably, they may include PEG, homopolymers or copolymers of PEG, monomethyl-substituted polymers (mPEG), and poly-amino acids such as poly-lysine, poly-aspartic acid, and poly-glutamic acid.

The variants of the glucagon derivative as described above also belong to the scope of the present invention.

In another aspect, the present invention provides polynucleotides encoding the glucagon derivatives described above.

The term "homology", as used herein for the polynucleotide, indicates the degree of similarity to a wild-type amino acid sequence and a wild-type nucleic acid sequence, and includes a gene sequence that is 75% or higher, preferably 85% or higher, more preferably 90% or higher, and even more preferably 95% or higher identical to the polynucleotide sequence encoding the glucagon derivatives. The homology evaluation may be done with the naked eye or using a commercially available program. Using a commercially available computer program, the homology between two or more sequences may be expressed as a percentage (%), and the homology (%) between adjacent sequences may be evaluated. The polynucleotide encoding the glucagon derivatives may be inserted into a vector and expressed to obtain a large amount of the glucagon derivatives.

For these recombinant expressions, the polynucleotides of the present invention are generally inserted into appropriate vectors to construct cloning vectors or recombinant vectors containing these polynucleotides, and these vectors also belong to the scope of the present invention.

As used herein, the term "recombinant vector" refers to a DNA construct including the sequence of a polynucleotide encoding a target peptide, which is operably linked to an appropriate regulatory sequence to enable the expression of the target peptide, e.g., a glucagon derivative, in a host cell. The regulatory sequence includes a promoter capable of initiating transcription, any operator sequence for the regulation of the transcription, a sequence encoding an appropriate mRNA ribosome-binding domain, and a sequence regulating the termination of transcription and translation. The recombinant vector, after being transformed into a suitable host cell, may be replicated or function irrespective of the host genome, or may be integrated into the host genome itself.

The recombinant vector used in the present invention may not be particularly limited as long as the vector is replicable in the host cell, and it may be constructed using any vector known in the art. Examples of the vector may include natural or recombinant plasmids, cosmids, viruses, and bacteriophages. For example, as a phage vector or cosmid vector, pWE15, M13, MBL3, MBL4, IXII, ASHII, t10, t11, Charon4A, Charon21A, etc., may be used; and as a plasmid vector, those based on pBR, pUC, pBluescriptII, pGEM, pTZ, pCL, pET, etc., may be used. The vectors that can be used in the present invention are not particularly limited but any known expression vector may be used.

The recombinant vector is used for the transformation of a host cell for producing glucagon derivatives of the present invention. Additionally, these transformed cells, as a part of the present invention, may be used for the amplification of nucleic acid fragments and vectors, or may be cultured cells or cell lines used in the recombinant production of glucagon derivatives of the present invention.

As used herein, the term "transformation" refers to a process of introducing a recombinant vector including a polynucleotide encoding a target protein into a host cell, thereby enabling the expression of the polynucleotide encoded by the protein in the host cell. For the transformed polynucleotide, it does not matter whether it is inserted into the chromosome of a host cell and located therein or located outside the chromosome, as long as it can be expressed in the host cell, and both cases are included.

Additionally, the polynucleotide includes DNA and RNA which encode the target protein. The polynucleotide may be inserted in any form insofar as it can be introduced into a host cell and expressed therein. For example, the polynucleotide may be introduced into a host cell in the form of an expression cassette. The expression cassette may conventionally include a promoter operably linked to the polynucleotide, a transcription termination signal, a ribosome-binding domain, and a translation termination signal. The expression cassette may be in the form of an expression vector capable of self-replication. Additionally, the polynucleotide may be introduced into a host cell as it is and operably linked to a sequence essential for its expression in the host cell, but is not limited thereto. Additionally, as used herein, the term "operably linked" refers to a functional connection between a promoter sequence, which initiates and mediates the transcription of the polynucleotide encoding the target protein of the present invention, and the above gene sequence, An appropriate host to be used in the present invention may not be particularly limited as long as it can express the polynucleotide of the present invention. Examples of the appropriate host may include bacteria belonging to the genus *Escherichia* such as *E. coli*, bacteria belonging to the genus *Bacillus* such as *Bacillus subtilis*, bacteria belonging to the genus *Pseudomonas* such as *Pseudomonas putida*, yeasts such as *Pichia pastoris, Saccharomyces cerevisiae*, and *Schizosaccharomyces pompe*, insect cells such as *Spodoptero frugipercia* (Sf9), and animal cells such as CHO, COS, and BSC.

In another aspect, the present invention provides a pharmaceutical composition for preventing or treating hypoglycemia or obesity containing the glucagon derivatives.

As used herein, the term "prevention" refers to any action resulting in suppression or delay of the onset of obesity by the administration of the glucagon derivatives or the pharmaceutical composition, and the term "treatment" refers to any action resulting in improvement in symptoms of obesity or the beneficial alteration by the administration of the glucagon derivatives or the pharmaceutical composition.

As used herein, the term "administration" refers to introduction of a particular material to a patient by an appropriate manner, and the composition may be administered via any of the common routes as long as the composition can arrive at a target tissue. For example, administration may be performed intraperitoneally, intravenously, intramuscularly, subcutaneously, intradermally, orally, topically, intranasally, intrapulmonarily, intrarectally, etc.

As used herein, the term "hypoglycemia" refers to an acute symptom of diabetes, in which blood glucose levels are lower than those of normal people, and in general, refers to a state when the blood glucose levels are 50 mg/dL or less. Hypoglycemia is frequently caused when a person who takes an oral hypoglycemic agent has eaten less than usual or has performed activities or exercised more than usual. In addition, hypoglycemia may occur due to the use of glucose level-lowering drugs, severe physical diseases, hormone deficiency such as adrenocortical hormones and glucagon, tumor in insulin-producing pancreas, insulin autoimmune syndrome, gastrectomy patients, inborn error of carbohydrate metabolism disorder, etc.

Symptoms of hypoglycemia include weakness, trembling, pale skin, cold sweat, dizziness, excitement, anxiety, pounding heart, empty stomach, headache, fatigue, etc. In the case of persistent hypoglycemia, it may lead to convulsion or seizure, and may cause shock and thus fainting.

As used herein, the term "obesity" refers to a medical condition with excess body fat in the body, and when a person having a body mass index (BMI; body mass (kg) divided by the square of the body height (m)) of 25 or higher is diagnosed as having obesity. Obesity generally occurs due to a long-term energy imbalance in which energy intake exceeds energy expenditure. Obesity is a metabolic disease that affects the entire body, which increases the risk of diabetes, hyperlipidemia, sexual dysfunction, arthritis, and cardiovascular disease, and in some cases, it is also associated with the occurrence of cancers.

The pharmaceutical composition of the present invention may contain a pharmaceutically acceptable carrier, excipient, or diluent. As used herein, the term "pharmaceutically acceptable" refers to the properties of having a sufficient amount to exhibit a therapeutic effect and not causing adverse effects, and may be easily determined by a skilled person in the art based on the factors well known in the medical field, such as the kind of disease, age, body weight, health status, sex, drug sensitivity of a patient, administration route, administration method, administration frequency, duration of treatment, a drug to be mixed or administered simultaneously in combination, etc.

The pharmaceutical composition of the present invention containing the glucagon derivative of the present invention may further contain a pharmaceutically acceptable carrier. The pharmaceutically acceptable carrier may include, for oral administration, a binder, a glidant, a disintegrant, an excipient, a solubilizing agent, a dispersant, a stabilizing agent, a suspending agent, a coloring agent, a flavoring agent, etc.; for injections, a buffering agent, a preserving agent, an analgesic, a solubilizing agent, an isotonic agent, a stabilizing agent, etc., which may be combined to be used; and for topical administrations, a base, an excipient, a lubricant, a preserving agent, etc., although it is not limited thereto.

The formulation type of the composition according to the present invention may be prepared variously by combining with a pharmaceutically acceptable carrier as described above. For example, for oral administration, the composition may be formulated into tablets, troches, capsules, elixirs, suspensions, syrups, wafers, etc. For injections, the composition may be formulated into single-dose ampoules or multidose containers. The composition may be also formulated into solutions, suspensions, tablets, capsules, and sustained-release formulations.

Meanwhile, examples of suitable carriers, excipients, and diluents may include lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinylpyrrolidone, water, methyl hydroxybenzoate, propyl hydroxybenzoate, talc, magnesium stearate, mineral oil, etc. Additionally, the composition may further contain a filler, an anti-coagulant, a lubricant, a humectant, a flavoring agent, a preservative, etc.

Additionally, the pharmaceutical composition of the present invention may be prepared in any formulation type selected from the group consisting of tablets, pills, powders, granules, capsules, suspensions, liquid medicine for internal use, emulsions, syrups, sterile injection solutions, non-aqueous solvents, lyophilized formulations, and suppositories.

Additionally, the composition may be formulated into a single dosage form suitable for the patient's body, and preferably is formulated into a preparation useful for peptide drugs according to the typical method in the pharmaceutical field so as to be administered by an oral or parenteral route, such as through skin, intravenously, intramuscularly, intraarterially, intramedullarily, intrathecally, intraventricularly, pulmonarily, transdermally, subcutaneously, intraperitoneally, intranasally, intragastrically, topically, sublingually, vaginally, or rectally, but is not limited thereto.

Additionally, the glucagon derivative may be used by blending with a variety of pharmaceutically acceptable carriers such as physiological saline or organic solvents. In order to increase the stability or absorptivity, carbohydrates such as glucose, sucrose, or dextrans, antioxidants such as ascorbic acid or glutathione, chelating agents, low molecular weight proteins, or other stabilizers may be used.

The administration dose and frequency of the pharmaceutical composition of the present invention are determined by the type of active ingredient(s), together with various factors such as the disease to be treated, administration route, patient's age, gender, and body weight, and severity of the disease.

The total effective dose of the composition of the present invention may be administered to a patient in a single dose, or may be administered for a long period of time in multiple doses according to a fractionated treatment protocol. In the pharmaceutical composition of the present invention, the content of active ingredient(s) may vary depending on the disease severity. Preferably, the total daily dose of the peptide of the present invention may be approximately 0.0001 µg to 500 mg per 1 kg of body weight of a patient. However, the effective dose of the glucagon derivative is determined considering various factors including patient's age, body weight, health conditions, gender, disease severity, diet, and excretion rate, in addition to administration route and treatment frequency of the pharmaceutical composition. In this regard, those skilled in the art may easily determine the effective dose suitable for the particular use of the pharmaceutical composition of the present invention. The pharmaceutical composition according to the present invention is not particularly limited to the formulation and administration route and mode, as long as it shows the effects of the present invention.

The pharmaceutical composition of the present invention shows excellent in viva duration of efficacy and titer, thereby remarkably reducing the number and frequency of administration thereof.

In particular, since the pharmaceutical composition of the present invention contains, as an active ingredient, a glucagon derivative having an altered pI different from that of native glucagon, it shows improved solubility and high stability according to the pH of a given solution, and thus the pharmaceutical composition of the present invention can be effectively used in the preparation of a stable glucagon formulation for treating hypoglycemia or obesity.

Furthermore, the pharmaceutical composition of the present invention may be administered alone or in combination with other pharmaceutical formulation(s) showing prophylactic or therapeutic effects on obesity. Additionally, the pharmaceutical composition of the present invention may further contain a pharmaceutical formulation showing prophylactic or therapeutic effects on obesity.

The pharmaceutical formulations showing prophylactic or therapeutic effects on obesity are not particularly limited, and may include a GLP-1 receptor agonist, a glucose-dependent insulinotropic peptide (GIP) receptor antagonist, a leptin receptor agonist, a DPP-IV inhibitor, a Y5 receptor antagonist, a melanin-concentrating hormone (MCH) receptor antagonist, a Y2/3/4 receptor agonist, an MC3/4 receptor agonist, a gastric/pancreatic lipase inhibitor, a 5HT2c agonist, a β3A receptor agonist, an amylin receptor agonist, a ghrelin antagonist and a ghrelin receptor antagonist, FGF1, an FGF21 receptor agonist, a cholecystokinin (CCK) receptor agonist, a pancreatic polypeptide (PP) receptor agonist, a dopamine reabsorption inhibitor, etc.

In still another aspect, the present invention provides a method for preventing or treating hypoglycemia or obesity, including administration of the glucagon derivative or the pharmaceutical composition containing the same to a subject.

As used herein, the term "subject" refers to those suspected of having hypoglycemia or obesity, which are mammals including humans, mice, and livestock animals having hypoglycemia or obesity, or with the possibility of having hypoglycemia or obesity. However, any subject to be treated with the glucagon derivatives or the pharmaceutical composition of the present invention is included without limitation. The pharmaceutical composition containing the glucagon derivative of the present invention may be administered to a subject suspected of having hypoglycemia or obesity, thereby treating the subject effectively. The hypoglycemia and obesity are the same as described above.

The therapeutic method of the present invention may include administration of the pharmaceutical composition containing the glucagon derivative at a pharmaceutically effective amount. Preferably, the total daily dose should be determined based on appropriate medical judgment by a physician and administered once or several times. In view of the objects of the present invention, the specific therapeutically effective dose for any particular patient may vary depending on various factors, such as the kind and degree of the response to be achieved, specific compositions including whether other agent(s) is (are) used therewith or not, the patient's age, body weight, health condition, gender, and diet, the time and route of administration, the secretion rate of the composition, duration of therapy, other drug(s) used in combination or simultaneously with the specific compositions, and similar factors well known in the medical art.

In still another aspect, the present invention provides a use of the glucagon derivatives in the preparation of pharmaceutical drugs for the prevention or treatment of hypoglycemia or obesity.

Advantageous Effects

The novel glucagon derivatives of the present invention have excellent stability and solubility according to the pH of a given solution by having a pI different from that of native glucagon. Therefore, when the novel glucagon derivatives of the present invention are used as a therapeutic agent for treating hypoglycemia, they can increase patient compliance. Additionally, the novel glucagon derivatives of the present invention are suitable for administration in combination with other anti-obesity agents, and thus they can be effectively used for preventing or treating hypoglycemia and obesity.

DETAILED DESCRIPTION OF THE INVENTION

Hereinafter, the present invention will be described in more detail with reference to the following Examples. However, these Examples are for illustrative purposes only and are not intended to limit the scope of the present invention.

Example 1: Production of a Cell Line Having a cAMP Response to Glucagon

PCR was performed using a region corresponding to an open reading frame (ORF) in cDNA (OriGene Technologies, Inc., USA) of human glucagon receptor gene as a template, and the following forward and reverse primers of SEQ ID NOS: 35 and 36, including each of the HindIII and EcoRI restriction sites.

In particular, PCR was performed for a total of 30 cycles using the following conditions: 95° C. denaturation for 60 seconds, annealing at 55° C. for 60 seconds, and extension at 68° C. for 30 seconds. The thus-obtained PCR product was electrophoresed in a 1.0% agarose gel, and a band with a size of 450 bp was obtained therefrom by elution.

```
Forward primer:
                                  (SEQ ID NO: 35)
5'-CAGCGACACCGACCGTCCCCCCGTACTTAAGGCC-3'

Reverse primer:
                                  (SEQ ID NO: 36)
5'-CTAACCGACTCTCGGGGAAGACTGAGCTCGCC-3'
```

The PCR product was cloned into a known animal cell expression vector, x0GC/dhfr, to prepare a recombinant vector x0GC/GCGR. CHO DG44 cell line cultured in DMEM/F12 (10% FBS) medium was transfected with the recombinant vector x0GC/GCGR using Lipofectamine, and selectively cultured in a selection medium containing 1 mg/mL. G418 and 10 nM Methotraxate. Single clone cell lines were selected therefrom by a limit dilution method, and among them, a cell line showing excellent cAMP response to glucagon in a concentration-dependent manner was finally selected therefrom.

Example 2: Synthesis of Glucagon Derivatives

It is widely known in the art that the solubility, activity, and stability of a protein in a solution can vary according to pI (Shaw, K. L. et al., Protein Science 10, pp 1206-1215, 2001). In order to prepare glucagon derivatives with improved physical properties, the amino acid sequence of native glucagon represented by SEQ ID NO: 1 was substituted with amino acid residues having positive and negative charges, and thereby glucagon derivatives were synthesized as shown in Table 1 below.

TABLE 1

| SEQ ID NO | Amino Acid Sequence | Ring Formation |
|---|---|---|
| SEQ ID NO: 1 | HSQGTFTSDYSKYLDSRRAQDFVQWLMNT | — |
| SEQ ID NO: 2 | HSQGTFTSDYSKYLDCDRAQDFVQWLMNT | — |

TABLE 1-continued

| SEQ ID NO | Amino Acid Sequence | Ring Formation |
|---|---|---|
| SEQ ID NO: 3 | HSQGTFTSDYSKYLDCERAQDFVQWLMNT | - |
| SEQ ID NO: 4 | HSQGTFTSDYSKYLDSCDAQDFVQWLMNT | - |
| SEQ ID NO: 5 | HSQGTFTSDYSKYLDSCEAQDFVQWLMNT | - |
| SEQ ID NO: 6 | HSQGTFTSDYSKYLDSCEADDFVQWLMNT | - |
| SEQ ID NO: 7 | YSQGTFTSDYSKYLDSCEADDFVQWLMNT | - |
| SEQ ID NO: 8 | YXQGTFTSDYSKYLDSCDAQDFVQWLINT | - |
| SEQ ID NO: 9 | YXQGTFTSDYSKYLDSCDAQDFVVWLINT | - |
| SEQ ID NO: 10 | YXQGTFTSDYSKYLDSCDADDFVVWLINT | - |
| SEQ ID NO: 11 | YXQGTFTSDYSKYLDEKCAKEFVQWLMNT | - |
| SEQ ID NO: 12 | YXQGTFTSDYSKYLDSRRAQDFVQWLMNT | - |
| SEQ ID NO: 13 | YXQGTFTSDYSCYLDEKRAKEFVQWLMNT | - |
| SEQ ID NO: 14 | YXQGTFTSDYSKYLDCKRAKEFVQWLMNT | - |
| SEQ ID NO: 15 | YXQGTFTSDYSKYLCEKRAQDFVVWLMNT | - |
| SEQ ID NO: 16 | YXQGTFTSDYSKYLDCRRAQVFVQWLMRT | - |
| SEQ ID NO: 17 | YXQGTFTSDYSKYLDCVRAQDFVQWLMRT | - |
| SEQ ID NO: 18 | YXQGTFTSDYSKYLDSRRACDFRLWLMNT | - |
| SEQ ID NO: 19 | YXQGTFTSDYSKYLCEKRAKEFVQWLMNT | ring formed |
| SEQ ID NO: 20 | YXQGTFTSDYSKYLDECRAKEFVQWLMNT | ring formed |
| SEQ ID NO: 21 | YXQGTFTSDYSKYLDEKCAKEFVQWLMNT | ring formed |
| SEQ ID NO: 22 | YXQGTFTSDYSKYLDEKRCKEFVQWLMNT | ring formed |
| SEQ ID NO: 23 | YXQGTFTSDYSKYCDEKRAKEFVQWLMNT | ring formed |
| SEQ ID NO: 24 | YXQGTFTSDYSKCLDEKRAKEFVQWLMNT | ring formed |
| SEQ ID NO: 25 | YXQGTFTSDYSKYLDEKRAKCFVQWLMNT | ring formed |
| SEQ ID NO: 26 | WXQGTFTSDYSKYLDECRAKDRVQWLMNT | ring formed |
| SEQ ID NO: 27 | YXQGTFVSDYSKYLDECRAKDRVQWLMNT | ring formed |
| SEQ ID NO: 28 | WXQGTFVSDYSKYLDECRAKDFVQWLMNT | ring formed |
| SEQ ID NO: 29 | YXQFTFTSDYSKCLDERRAKDFVQWLMNT | ring formed |
| SEQ ID NO: 30 | WXQGTFTSDYSKCLDERRAKDFVQWLMNT | ring formed |
| SEQ ID NO: 31 | YXQGTFTSDYSKYLDCKRAKEFVQWLMNT | ring formed |
| SEQ ID NO: 32 | -SQGTFTSDYSKYLDECRAKEFVQWLMNT | ring formed |
| SEQ ID NO: 33 | WXQGTFTSDYSKYCDERRAKEFVQWLMNT | ring formed |
| SEQ ID NO: 34 | YXQGTFTSDYSKYCDERRAKEFVQWLMNT | ring formed |

Regarding the SEQ ID NOS: 8 to 31 and 33 to 34 shown in Table 1, the amino acid represented by X represents a non-native amino acid, aminoisobutyric acid (Aib); "-" in the amino acid sequence of SEQ ID NO: 32 means that no amino acid residue is present on the corresponding position; and the two bold and underlined amino acid residues represent formation of a ring between the two amino acid residues.

Example 3: Measurement of pI of Glucagon Derivatives

In order to measure the improved physical properties of glucagon derivatives synthesized in Example 2, pI values were calculated based on the amino acid sequences using the pI/Mw tool (expasy.org/tools/pi_tool.html; Gasteiger et al., 2003) in the ExPASy server.

TABLE 2

| Glucagon Derivatives | pI |
| --- | --- |
| SEQ ID NO: 1 | 6.8 |
| SEQ ID NO: 2 | 4.56 |
| SEQ ID NO: 3 | 4.66 |
| SEQ ID NO: 4 | 4.13 |
| SEQ ID NO: 5 | 4.22 |
| SEQ ID NO: 6 | 4.03 |
| SEQ ID NO: 7 | 3.71 |
| SEQ ID NO: 8 | 3.77 |
| SEQ ID NO: 9 | 3.77 |
| SEQ ID NO: 10 | 3.66 |
| SEQ ID NO: 11 | 4.78 |
| SEQ ID NO: 12 | 6.04 |
| SEQ ID NO: 13 | 4.78 |
| SEQ ID NO: 14 | 8.12 |
| SEQ ID NO: 15 | 6.11 |
| SEQ ID NO: 16 | 9.11 |
| SEQ ID NO: 17 | 6.03 |
| SEQ ID NO: 18 | 8.15 |
| SEQ ID NO: 19 | 8.12 |
| SEQ ID NO: 20 | 4.78 |
| SEQ ID NO: 21 | 4.78 |
| SEQ ID NO: 22 | 6.20 |
| SEQ ID NO: 23 | 6.20 |
| SEQ ID NO: 24 | 6.21 |
| SEQ ID NO: 25 | 8.12 |
| SEQ ID NO: 26 | 4.68 |
| SEQ ID NO: 27 | 4.68 |
| SEQ ID NO: 28 | 4.68 |
| SEQ ID NO: 29 | 6.15 |
| SEQ ID NO: 30 | 4.44 |
| SEQ ID NO: 31 | 8.12 |
| SEQ ID NO: 32 | 4.78 |
| SEQ ID NO: 33 | 6.21 |
| SEQ ID NO: 34 | 6.21 |

As shown in Table 2 above, while the native glucagon of SEQ ID NO: 1 had a pI of 6.8, the glucagon derivatives according to the present invention showed pI values in the range of from about 4 to about 9, thus showing improved physical properties. Since the glucagon derivatives according to the present invention have pI values different from that of native glucagon, they can exhibit improved solubility and higher stability according to the pH conditions of a given solution.

Accordingly, when the glucagon derivatives according to the present invention are used as a therapeutic agent for treating hypoglycemia, they can improve patient compliance, and are also suitable for administration in combination with other anti-obesity agents, e.g., a GLP-1 receptor antagonist, a glucose-dependent insulinotropic peptide (GIP) receptor antagonist, etc., and thus can be effectively used as a therapeutic agent for treating hypoglycemia and obesity.

Those of ordinary skill in the art will recognize that the present invention may be embodied in other specific forms without departing from its spirit or essential characteristics. The described embodiments are to be considered in all respects only as illustrative and not restrictive. The scope of the present invention is, therefore, indicated by the appended claims rather than by the foregoing description. All changes which come within the meaning and range of equivalency of the claims are to be embraced within the scope of the present invention.

The invention claimed is:

1. A peptide comprising the amino acid sequence of the following General Formula 1:

(General Formula 1)
X1-X2-QGTF-X7-SDYS-X12-X13-X14-X15-X16-X17-X18-X19-X20-X21-F-X23-X24-W-L-X27-X28-T wherein, in General Formula 1, X1 is desamino-histidine, N-dimethyl-histidine, β-hydroxyimidazopropionic acid, 4-imidazoacetic acid, β-carboxyimidazopropionic acid, tryptophan, tyrosine, or deleted;

X2 is α-methyl-glutamic acid, aminoisobutyric acid (Aib), D-alanine, glycine, Sar(N-methylglycine), serine, or D-serine;

X7 is threonine or valine;
X12 is lysine or cysteine;
X13 is tyrosine or cysteine;
X14 is leucine or cysteine;
X15 is aspartic acid, glutamic acid, or cysteine;
X16 is glutamic acid, aspartic acid, serine, α-methyl-glutamic acid, or cysteine;
X17 is aspartic acid, glutamic acid, lysine, arginine, serine, valine, or cysteine;
X18 is aspartic acid, glutamic acid, arginine, or cysteine;
X19 is alanine or cysteine;
X20 is lysine, glutamic acid, glutamine, aspartic acid, or cysteine;
X21 is aspartic acid, glutamic acid, valine, or cysteine;
X23 is valine or arginine;
X24 is valine, leucine, or glutamine;
X27 is isoleucine or methionine; and
X28 is arginine, with the proviso that the amino acid sequence of General Formula 1 excludes SEQ ID NO: 1 and SEQ ID NO: 12.

2. The peptide of claim 1, wherein, in the amino acid sequence of General Formula 1, X1 is tryptophan, tyrosine, or deleted;
X2 is serine or aminoisobutyric acid (Aib);
X7 is threonine or valine;
X12 is lysine or cysteine;
X13 is tyrosine or cysteine;
X14 is leucine or cysteine;
X15 is aspartic acid or cysteine;
X16 is glutamic acid, aspartic acid, serine, or cysteine;
X17 is aspartic acid, glutamic acid, lysine, arginine, valine, or cysteine;
X18 is aspartic acid, glutamic acid, arginine, or cysteine;
X19 is alanine or cysteine;
X20 is lysine, glutamic acid, glutamine, aspartic acid, or cysteine;
X21 is aspartic acid, glutamic acid, valine, or cysteine;
X23 is valine or arginine;
X24 is valine, leucine, or glutamine;
X27 is isoleucine or methionine; and
X28 is arginine, with the proviso that the amino acid sequence of General Formula 1 excludes SEQ ID NO: 1 and SEQ ID NO: 12.

3. A pharmaceutical composition comprising the peptide according to claim 2 as an active ingredient.

4. A composition, comprising the peptide according to claim 2 as an active ingredient.

5. The peptide of claim 1, which comprises the amino acid sequence represented by SEQ ID NO: 16 or 17.

6. A pharmaceutical composition comprising the peptide according to claim 5 as an active ingredient.

7. A composition, comprising the peptide according to claim 5 as an active ingredient.

8. A pharmaceutical composition comprising the peptide according to claim 1 as an active ingredient.

9. The pharmaceutical composition according to claim 8, further comprising a pharmaceutically acceptable carrier.

10. A composition, comprising the peptide according to claim 1 as an active ingredient.

* * * * *